(12) United States Patent
Kishimoto et al.

(10) Patent No.: US 6,537,790 B1
(45) Date of Patent: Mar. 25, 2003

(54) ESTERASE GENES AND USES OF THE SAME

(75) Inventors: Kae Kishimoto, Kobe (JP); Yuko Kobayashi, Toyonaka (JP); Yoshiki Takashima, Nishinomiya (JP); Ayumu Inoue, Nishinomiya (JP)

(73) Assignee: Sumitomo Chemical Company, Limited, Osaka (JP)

( * ) Notice: Subject to any disclaimer, the term of this patent is extended or adjusted under 35 U.S.C. 154(b) by 76 days.

(21) Appl. No.: 09/585,468

(22) Filed: Jun. 2, 2000

(30) Foreign Application Priority Data

Jun. 4, 1999 (JP) ............................................. 11-158199

(51) Int. Cl.⁷ ............................. C12N 9/16; C07H 27/04
(52) U.S. Cl. ...................................... 435/196; 536/23.2
(58) Field of Search ........................... 435/196; 536/23.2

(56) References Cited

FOREIGN PATENT DOCUMENTS

| WO | WO 90/09446 | 8/1990 |
| WO | WO 94/14963 | 7/1994 |
| WO | WO 94/14964 | 7/1994 |
| WO | WO 95/03421 | 2/1995 |
| WO | WO 98/02568 | 1/1998 |

OTHER PUBLICATIONS

*Current Protocolols in Protein Science*, vol. 1, John Wiley & Sons, Inc. (1997), pp. 5.2.11–6.1.9.

*Primary Examiner*—Ponnathapu Achutamurthy
*Assistant Examiner*—Malgorzata A Walicka
(74) *Attorney, Agent, or Firm*—Sughrue Mion, PLLC

(57) ABSTRACT

The present invention provides a novel gene encoding a protein having an excellent catalyst ability for producing (S)-N-substituted cyclic imino acid represented by formula (2):

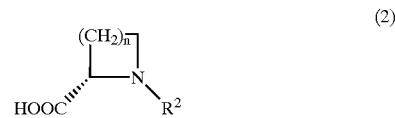

and provides a novel method for producing (S)-N-substituted cyclic imino acid represented by formula (2) by an asymmetric hydrolization of the N-substituted cyclic imino acid ester represented by formula (1):

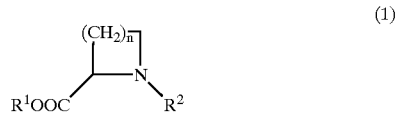

in a manner of gene engineering technology utilizing the novel gene provided.

3 Claims, 1 Drawing Sheet

SEQUENCE LISTING

<160> NUMBER OF SEQ ID NOS: 5

<210> SEQ ID NO 1
<211> LENGTH: 255
<212> TYPE: PRT
<213> ORGANISM: Aspergillus flavus

<400> SEQUENCE: 1

Met His Leu Pro Ile Lys Thr Leu Phe Val Ser Leu Leu Gly Ala Ser
 1               5                  10                  15

```
Val Leu Ala Arg Pro Leu Pro Asn Asp Ala Leu Val Glu Arg Asn Ala
         20                  25                  30

Pro Leu Asn Glu Phe Leu Ser Val Leu Leu Ser His Leu Pro Ala Ile
         35                  40                  45

Asn Gly Ser Ile Thr Ala Val Ser Gly Leu Ile Thr Asp Phe Asp Gln
 50                  55                  60

Leu Leu Ala Asp Ile Thr Gly Ala Gln Thr Thr Leu Asn Gly Phe Thr
 65                  70                  75                  80

Gly Ala Cys Thr Asp Tyr Thr Val Leu Phe Ala Arg Gly Thr Ser Glu
                 85                  90                  95

Pro Gly Asn Val Gly Val Leu Val Gly Pro Leu Ala Glu Ala Phe
             100                 105                 110

Glu Gly Ala Val Gly Ala Ser Ala Leu Ser Phe Gln Gly Val Asn Gly
         115                 120                 125

Tyr Ser Ala Ser Val Glu Gly Tyr Leu Ala Gly Glu Ala Ala Gly
             130                 135                 140

Ser Lys Ala Met Ala Ser Gln Ala Ser Asp Ile Leu Ser Lys Cys Pro
145                 150                 155                 160

Asp Thr Lys Leu Val Met Ser Gly Tyr Ser Gln Gly Cys Gln Ile Val
                 165                 170                 175

His Asn Ala Val Glu Gln Leu Pro Ala Glu His Ala Ser Lys Ile Ser
             180                 185                 190

Ser Val Leu Leu Phe Gly Asp Pro Tyr Lys Gly Lys Ala Leu Pro Asn
         195                 200                 205

Val Asp Ala Ser Arg Val His Thr Val Cys His Ala Gly Asp Thr Ile
         210                 215                 220

Cys Glu Asn Ser Val Ile Ile Leu Pro Ala His Leu Thr Tyr Ala Val
225                 230                 235                 240

Asp Val Ala Ser Ala Ala Asp Phe Ala Val Ala Ala Lys Asn
                 245                 250                 255

<210> SEQ ID NO 2
<211> LENGTH: 798
<212> TYPE: DNA
<213> ORGANISM: Aspergillus flavus
<220> FEATURE:
<221> NAME/KEY: CDS
<222> LOCATION: (1)..(768)

<400> SEQUENCE: 2 atg cat ctt cct atc aag act ctc ttt gtc tct ctc ctc gga gcc agc      48
Met His Leu Pro Ile Lys Thr Leu Phe Val Ser Leu Leu Gly Ala Ser
 1               5                  10                  15 gtt ctc gca cgc cct ctt ccc aat gat gct ctc gtt gag aga aac gct     96
Val Leu Ala Arg Pro Leu Pro Asn Asp Ala Leu Val Glu Arg Asn Ala
                 20                  25                  30 ccc cta aac gag ttc ctc agc gtc ctt ctg tct cat ttg cct gcc att    144
Pro Leu Asn Glu Phe Leu Ser Val Leu Leu Ser His Leu Pro Ala Ile
         35                  40                  45 aac ggc tct atc act gcg gtg tcg ggt ctg atc acc gat ttt gat caa    192
Asn Gly Ser Ile Thr Ala Val Ser Gly Leu Ile Thr Asp Phe Asp Gln
 50                  55                  60 ttg ctt gct gac atc acc ggt gct caa aca acc ctg aat gga ttt act    240
Leu Leu Ala Asp Ile Thr Gly Ala Gln Thr Thr Leu Asn Gly Phe Thr
 65                  70                  75                  80 ggt gcc tgc acg gat tac acc gtt ctc ttc gcc cgc gga acc agt gag    288
Gly Ala Cys Thr Asp Tyr Thr Val Leu Phe Ala Arg Gly Thr Ser Glu
```

```
ccc gga aac gtt ggt gtc ctc gtc gga cct cct ctt gct gag gcg ttt      336
Pro Gly Asn Val Gly Val Leu Val Gly Pro Pro Leu Ala Glu Ala Phe
            100                 105                 110 gag gga gcc gtc ggt gcg tcc gcc ttg agc ttc cag ggt gtc aac ggc      384
Glu Gly Ala Val Gly Ala Ser Ala Leu Ser Phe Gln Gly Val Asn Gly
        115                 120                 125 tat tct gca tct gtc gag gga tat ttg gct gga ggt gaa gcc gct ggc      432
Tyr Ser Ala Ser Val Glu Gly Tyr Leu Ala Gly Gly Glu Ala Ala Gly
130                 135                 140 agc aag gca atg gca tct cag gcc agc gac att ctc tcc aag tgt ccc      480
Ser Lys Ala Met Ala Ser Gln Ala Ser Asp Ile Leu Ser Lys Cys Pro
145                 150                 155                 160 gac acc aag ctt gtc atg agt ggc tat tcc cag ggc tgc cag att gtt      528
Asp Thr Lys Leu Val Met Ser Gly Tyr Ser Gln Gly Cys Gln Ile Val
                165                 170                 175 cac aat gcc gtt gag caa ctt cct gcg gaa cac gca agc aag atc agc      576
His Asn Ala Val Glu Gln Leu Pro Ala Glu His Ala Ser Lys Ile Ser
            180                 185                 190 agc gtc ctc ctt ttc gga gac cca tac aag ggc aag gct ctc ccc aac      624
Ser Val Leu Leu Phe Gly Asp Pro Tyr Lys Gly Lys Ala Leu Pro Asn
        195                 200                 205 gtt gat gct tcc cgc gtc cac act gtg tgc cac gct gga gac act att      672
Val Asp Ala Ser Arg Val His Thr Val Cys His Ala Gly Asp Thr Ile
210                 215                 220 tgc gag aac agc gtt att att ctg ccc gct cac ttg acc tac gct gtt      720
Cys Glu Asn Ser Val Ile Ile Leu Pro Ala His Leu Thr Tyr Ala Val
225                 230                 235                 240 gat gtg gct tct gcg gct gac ttc gct gtt gcg gct gca aag aac taa      768
Asp Val Ala Ser Ala Ala Asp Phe Ala Val Ala Ala Lys Asn
                245                 250                 255 attacgataa gggctccatg ttcactgtaa                                     798

<210> SEQ ID NO 3
<211> LENGTH: 33
<212> TYPE: PRT
<213> ORGANISM: Escherichia coli

<400> SEQUENCE: 3

Met Lys Gln Ser Thr Ile Ala Leu Ala Leu Leu Pro Leu Leu Phe Thr
 1               5                  10                  15

Pro Val Ala Asn Ala Ala Pro Thr Ser Asn Pro Ala Gln Glu Leu Glu
            20                  25                  30

Ala
 33

<210> SEQ ID NO 4
<211> LENGTH: 20
<212> TYPE: PRT
<213> ORGANISM: Aspergillus flavus
<220> FEATURE:
<221> NAME/KEY: UNSURE
<222> LOCATION: 6
<223> OTHER INFORMATION: Xaa=Glu or Ala
<221> NAME/KEY: UNSURE
<222> LOCATION: 13
<223> OTHER INFORMATION: Xaa=Ser or Gly
<221> NAME/KEY: UNSURE
<222> LOCATION: 19
<223> OTHER INFORMATION: Xaa is unknown
<221> NAME/KEY: UNSURE
<222> LOCATION: 20
<223> OTHER INFORMATION: Xaa=His or Gly
```

```
<400> SEQUENCE: 4

Asn Ala Pro Leu Glx Xaa Phe Leu Ser Val Leu Leu Xaa His Leu Pro
 1               5                   10                  15

Ala Ile Xaa Xaa
            20

<210> SEQ ID NO 5
<211> LENGTH: 17
<212> TYPE: DNA
<213> ORGANISM: Artificial Sequence
<220> FEATURE:
<223> OTHER INFORMATION: Designed oligonucleotide primer for PCR

<400> SEQUENCE: 5
aacgaattcc tsagygt                                               17
```

ESTERASE GENES AND USES OF THE SAME

BACKGROUND OF THE INVENTION

1. Field of the Invention

The present invention relates to an esterase gene and a use of the same.

2. Description of the Prior Art

An (S)-N-substituted cyclic imino acid represented by the general formula (2):

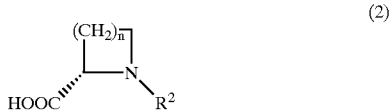

(2)

wherein $R^2$ is an aralkyl group having 7 to 19 carbon atoms; an alkylcarbonyl group having 2 to 5 carbon atoms, an arylcarbonyl group having 7 to 13 carbon atoms; an alkyloxycarbonyl group having 2 to 9 carbon atoms; an aralkyloxycarbonyl group having 8 to 10 carbon atoms; an alkenyloxycarbonyl group having 3 to 9 carbon atoms; an aryloxycarbonyl group having 7 to 13 carbon atoms; an alkyl group having 1 to 8 carbon atoms; an alkenyl group having 2 to 8 carbon atoms; an aryl group having 6 to 12 carbon atoms; or an arylsulfonyl group having 6 to 12 carbon atoms, and one or more hydrogen atoms bound to an aromatic ring of said aralkyl, arylcarbonyl, aralkyloxycarbonyl, aryloxycarbonyl, aryl or arylsulfonyl group may optionally be substituted with at least one selected from an alkyl group having 1 to 8 carbon atoms, an alkoxy group having 1 to 8 carbon atoms, a halogen atom and a nitro group, and one or more hydrogen atoms in said alkylcarbonyl, alkyloxycarbonyl or alkyl group may optionally be substituted with at least one selected from an alkoxy group having 1 to 8 carbon atoms, a halogen atom and a nitro group;

and n is 1 or 2.

Compounds of formula (2) (hereinafter referred to sometimes as the (S)-cyclic imino acid (2)) are useful intermediates for a pharmaceutical.

Among such (S)-cyclic imino acid (2) compounds is an N-substituted-azetidine-2-carboxylic acid represented by the general formula (3):

(3)

wherein $R^2$ is a hydrogen atom or a protective group, and * is an asymmetric carbon atom. N-substituted-azetidine-2-carboxylic acid is produced biologically using a biocatalyst, which is an enzyme derived from a microorganism such as *Candida antarctica, Penicillium camembertii, Rhizopus chinensis, Rhizopus japonicus, Mucor javanicus, Mucor miehei, Bacillus subtilis, Candida rugosa, Candida cylindracea, Pseudomonas cepacia, Bacillus licheniformis, Bacillus sp.*, and *Aspergillus niger*, as described in JP-A-11-46784 (1999). The optical purity (% ee) of the enzyme, an intrinsic property determined based on the molecular structure of the enzyme, is also described in JP-A-11-46784 (1999).

SUMMARY OF THE INVENTION

An objective of the present invention is to provide a novel gene encoding a protein having an excellent catalyst ability for producing (S)-cyclic imino acid (2) and to provide a novel method for producing (S)-cyclic imino acid (2) by an asymmetric hydrolization of the N-substituted cyclic imino acid ester represented by the general formula (1):

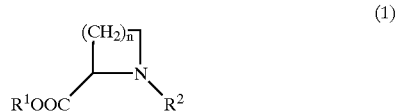

(1)

wherein $R^1$ is an alkyl group having 1 to 8 carbon atoms, an aralkyl group having 7 to 19 carbon atoms, an alkenyl group having 2 to 5 carbon atoms or an aryl group having 6 to 12 carbon atoms, and one or more hydrogen atoms in said alkyl group may optionally be substituted with at least one selected from an alkoxyl group having 1 to 8 carbon atoms, a halogen atom and a nitro group and one or more hydrogen atoms bound to an aromatic ring in said aralkyl or aryl group may optionally be substituted with at least one selected from an alkyl group having 1 to 8 carbon atoms, an alkoxy group having 1 to 8 carbon atoms, a halogen atom or a nitro group;

and $R^2$ and n are defined as described above (hereinafter referred to sometimes as the cyclic imino acid ester (1)) in a manner of gene engineering technology utilizing the novel gene provided.

Accordingly, Applicants have found a novel gene encoding a protein having an excellent catalyst ability for producing (S)-cyclic imino acid (2), thereby arriving at the present invention.

Scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

DETAILED DESCRIPTION OF THE INVENTION

Figure 1:
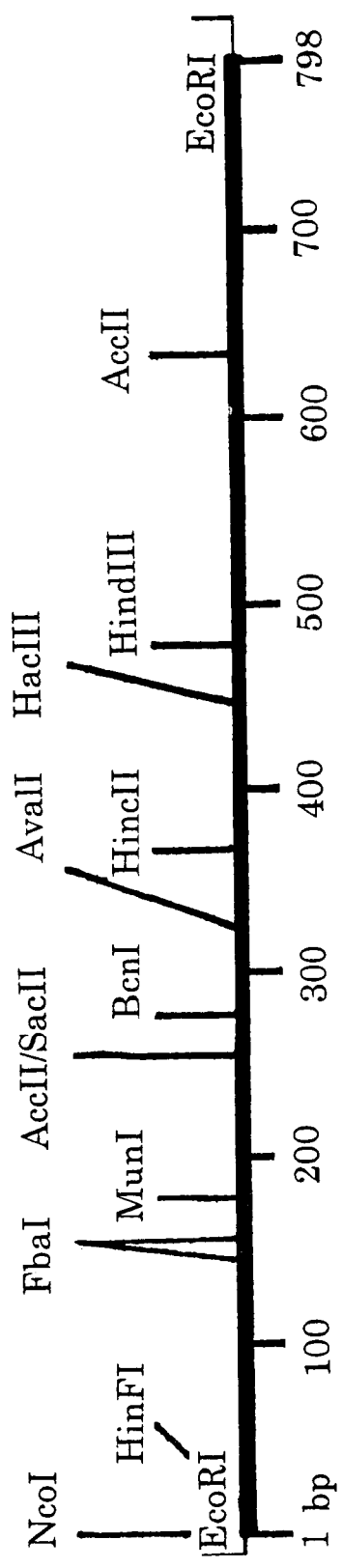
FIG. 1 shows a restriction enzyme map of the gene of the present invention which is contained in plasmid pYHN1.

The gene of the present invention encompasses a gene comprising any one of the following nucleotide sequences:

(i) the nucleotide sequence represented by SEQ ID NO:2;

(ii) a nucleotide sequence encoding the amino acid sequence represented by SEQ ID NO:1;

(iii) a nucleotide sequence which encodes an amino acid sequence of a protein capable of hydrolyzing a racemic ethyl N-benzylazetidine-2-carboxylate asymmetrically and producing an (S)-N-benzylazetidine-2-carboxylic acid predominantly and which consists of a part of the nucleotide sequence represented by SEQ ID NO:2; (More specifically, for example, a nucleotide sequence represented by Nucleotide No.103 to 765 in the nucleotide sequence represented by SEQ ID NO:2; a nucleotide sequence represented by Nucleotide No.235 to 765 in the nucleotide sequence represented by SEQ ID NO:2; a nucleotide sequence encoding an amino acid sequence represented by Amino Acid No.35 to 255 in the amino acid sequence represented by SEQ ID NO:1; a nucleotide sequence encoding an amino acid sequence represented by Amino Acid No.79 to 255 in the amino acid sequence represented by SEQ ID NO:1)

(iv) a nucleotide sequence which encodes an amino acid sequence of a protein capable of hydrolyzing a racemic ethyl N-benzylazetidine-2-carboxylate asymmetrically and producing an (S)-N-benzylazetidine-2-carboxylic acid predominantly and which hybridizes under a stringent condition with a DNA consisting of a nucleotide sequence encoding the amino acid sequence represented by SEQ ID NO:1;

(v) a nucleotide sequence which encodes an amino acid sequence of a protein capable of hydrolyzing a racemic ethyl N-benzylazetidine-2-carboxylate asymmetrically and producing an (S)-N-benzylazetidine-2-carboxylic acid predominantly and which encodes an amino acid sequence of a protein having a molecular weight of about 25,000 daltons determined by an SDS-PAGE;

(vi) a nucleotide sequence which encodes an amino acid sequence of a protein capable of hydrolyzing a racemic ethyl N-benzylazetidine-2-carboxylate asymmetrically and producing an (S)-N-benzylazetidine-2-carboxylic acid predominantly and which has a nucleotide homology of 60% or higher with a nucleotide sequence represented by Nucleotide No.235 to 765 in the nucleotide sequence represented by SEQ ID NO:2; and, (vii) a nucleotide sequence of a DNA which is amplified by a PCR using as a primer an oligonucleotide allowing a DNA having a nucleotide sequence represented by Nucleotide No.235 to 765 in the nucleotide sequence represented by SEQ ID NO:2 to be capable of being amplified and as a template chromosomal DNA derived from a microorganism belong to *Aspergillus flavus;* and the like.

The gene described above may be a naturally-occurring gene or a gene created for example by introducing a variation into a naturally-occurring gene by means of a site directed mutagenesis or a random mutagenesis. When a naturally-occurring gene is screened, a microorganism capable of hydrolyzing a racemic ethyl ester N-benzylazetidine-2-carboxylate asymmetrically and producing an (S)-N-benzylazetidine-2-carboxylic acid predominantly may be subjected to screening. As a preferred subject is exemplified a microorganism belonging to *Aspergillus flavus*.

The gene of the present invention has a nucleotide sequence which encodes an amino acid sequence of a protein having the ability to catalyze an ester asymmetric hydrolysis, at least an ability of hydrolyzing a racemic ethyl ester N-benzylazetidine-2-carboxylate as a representative substrate asymmetrically and producing an (S)-N-benzylazetidine-2-carboxylic acid predominantly. For example, a reaction mixture is prepared by adding 0.02 g of a racemic ethyl ester N-benzylazetidine-2-carboxylate and 1.0 mL of methyl-t-butylether to 3.5 mL of a 100 mM potassium phosphate buffer (pH7.0) containing a protein having an amino acid sequence corresponding to a nucleotide sequence of the gene of the present invention, and then incubated at about 30° C. to about 35° C. for about 1 hour to about 24 hours with shaking, and a resultant reaction mixture is centrifuged (12,000 rpm, 5 minutes) to obtain an aqueous phase, which is then examined to determine the amount of optically active N-benzylazetidine-2-carboxylic acid content, thereby determining whether the intended ability is present or not. A method for quantifying an optically active N-benzylazetidine-2-carboxylic acid is exemplified in Examples described later.

In the gene of the present invention, a DNA "which hybridizes under a stringent condition with a DNA consisting of a nucleotide sequence encoding the amino acid sequence represented by SEQ ID NO:1" means a DNA (1) which forms a DNA-DNA hybrid with a DNA consisting of a nucleotide sequence encoding the amino acid sequence represented by SEQ ID NO: 1 by means of hybridization at 65° C. at a high ion concentration using, for example, 6×SSC (900 mM sodium chloride, 90 mM sodium citrate) and (2) which allows the resultant hybrid to be maintained even after being incubated for 30 minutes at 65° C. at a low ion concentration using, for example, 0.1×SSC (15 mM sodium chloride, 1.5 mM sodium citrate), when it is subjected to a southern hybridization described for example in "Cloning and Sequence" (Supervised by WATANABE and edited by SUGIURA, 1989, NOSONBUNKASHA). Typically, a DNA having a nucleotide sequence encoding the amino acid sequence represented by SEQ ID NO:1 or a DNA having a nucleotide sequence encoding the amino acid sequence represented by SEQ ID NO:1 in which a part of the nucleotide sequence is deleted, substituted or added may be contemplated. Such DNAs may be a DNA cloned from a wild type organism, a DNA obtained by an artificial deletion, substitution or addition of a nucleotide in such cloned DNA, or a DNA which is synthesized artificially.

More specifically, (a) a DNA having a nucleotide sequence encoding an amino acid sequence represented by Amino Acid No.79 to 255 in the amino acid sequence represented by SEQ ID NO:1 or a nucleotide sequence derived therefrom by adding an initiation codon (ATG) to its 5' terminal, (b) a DNA having a nucleotide sequence represented by Nucleotide No.235 to 765 in the nucleotide sequence represented by SEQ ID NO:2 or a nucleotide sequence derived therefrom by adding an initiation codon (ATG) to its 5' terminal, (c) a DNA having a nucleotide sequence encoding an amino acid sequence represented by Amino Acid No.35 to 255 in the amino acid sequence represented by SEQ ID NO:1 or a nucleotide sequence derived therefrom by adding an initiation codon (ATG) to its 5' terminal, (d) a DNA having a nucleotide sequence represented by Nucleotide No.103 to 765 in the nucleotide sequence represented by SEQ ID NO:2 or a nucleotide sequence derived therefrom by adding an initiation codon (ATG) to its 5' terminal, (e) a DNA-having a nucleotide sequence encoding the amino acid sequence represented by SEQ ID NO:1, a DNA having the nucleotide sequence represented by SEQ ID NO:2, and the like.

In the gene of the present invention, a nucleotide homology of 60% or higher with a nucleotide sequence represented by Nucleotide No.235 to 765 in the nucleotide sequence represented by SEQ ID NO:2 means a homology in terms of the entire sequence represented by SEQ ID NO:2. Preferably, it is a nucleotide homology of 80% or higher.

A DNA of the gene of the present invention may for example be prepared as follows. First, chromosomal DNA or a cDNA is prepared from a microorganism belonging to for example *Aspergillus flavus* in accordance with conventional gene engineering methods (for example a method described in "NEW CELL ENGINEERING EXPERIMENT PROTOCOL" (ed. By CARCINOSTATIC RESEARCH DIVISION of MEDICAL RESEARCH INSTITUTE of TOKYO UNIVERSITY, SHUJUNSHA, 1993), and the resultant DNA is used as a template to perform a PCR under the condition described below using as a primer an oligonucleotide that would produce a DNA having a nucleotide sequence represented by Nucleotide No.235 to 765 in the nucleotide sequence represented by SEQ ID NO:2, thereby amplifying a DNA having a nucleotide sequence represented by Nucleotide No.235 to 765 in the nucleotide sequence represented by SEQ ID NO:2.

More specifically, for example, an oligonucleotide having a nucleotide sequence represented by Nucleotide No.1 to 27 in the nucleotide sequence represented by SEQ ID NO:2 and an oligonucleotide having a nucleotide sequence complementary to a nucleotide sequence represented by Nucleotide No.784 to 798 in the nucleotide sequence represented by SEQ ID NO:2 are used as primers to perform a PCR under the condition described below, thereby amplifying a DNA having a nucleotide sequence encoding the amino acid sequence represented by SEQ ID NO:1.

A condition of a PCR may involve the use of 100 µl of a reaction solution containing 4 dNTPs each at the final concentration of 0.2 mM, 2 primers each at 5 pmol, a Taq polymerase Gold (manufactured by Perkin Elmer KIKOTECH) at 2.5 U and a cDNA as a template, which is mounted on a PCR device and heated at 98° C. (7 minutes) and then subjected to 20 cycles of an incubation at 97° C. (0.3 minutes)-45° C. (1 minute)-72° C. (2 minute), followed by 20 cycles of an incubation at 94° C. (1 minute)-50° C. (0.3 minutes)-75° C. (2.5 minutes), followed by the incubation at 70° C. (7 minutes). The 5'-terminal of a primer used in such PCR may for example be attached to a restriction enzyme recognition sequence.

When a DNA library obtained by inserting a chromosomal DNA or a cDNA into a vector is used as a template, an oligonucleotide having a nucleotide sequence selected from the nucleotide sequences encoding the amino acid sequence represented by SEQ ID NO:1 (for example, an oligonucleotide consisting of a nucleotide sequence of about 14 nucleotides or more from the 5' terminal of a nucleotide sequence encoding the amino acid sequence represented by SEQ ID NO:1) and an oligonucleotide of about 14 nucleotides or more consisting of a nucleotide sequence complementary to a nucleotide sequence near the DNA insertion site in a vector used in the construction of a library, are used as primers to perform a PCR, thereby amplifying a DNA of a gene of the invention.

Alternatively, a DNA consisting of a nucleotide sequence encoding an amino acid sequence in which one or more of the amino acids in the amino acid sequence represented by SEQ ID NO:1 is deleted, substituted or added may be prepared as follows.

For example, a random mutation may be introduced into a DNA consisting of the nucleotide sequence represented by SEQ ID NO:2 by the method described in A. Greener, M. Callahan, Strategies, 1994, Vol.7, page 32–34 and the like. Alternatively, a mutation may be introduced site-specifically into a DNA consisting of the nucleotide sequence represented by SEQ ID NO:2 in accordance with a gapped duplex method described in W. Kramer et al., Nucleic Acids Research, 1984, Vol. 12, p.9441 or W. Kramer, H. J. Frits, Methods in Enzymology, 1987, Vol.154, p.350 and the like or a Kunkel method described in T. A. Kunkel, Proc. of Natl. Acad. Sci. USA, 1985, Vol.82, p.488 or T. A. Kunkel et al., Methods in Enzymology, 1987, Vol.154, p.367 and the like. A DNA consisting of a nucleotide sequence in which one or more of the nucleotides in the nucleotide sequence represented by SEQ ID NO:2 is deleted, substituted or added may also be amplified by performing a PCR using a DNA consisting of the nucleotide sequence represented by SEQ ID NO:2 as a template and an oligonucleotide having a nucleotide sequence in which one or more of the nucleotides in a part of the nucleotide sequence represented by SEQ ID NO:2 is deleted, substituted or added as a primer.

Furthermore, a DNA having a nucleotide sequence in which a part of the nucleotide sequence represented by SEQ ID NO:2 is deleted may be prepared by the method described in S. Henikoff, et al., Gene, 1984, Vol.28, p.351 or C. Yanisch-Perron et al., Gene, 1985, Vol.33, p.103 and the like. From the DNAs thus obtained, a DNA having a nucleotide sequence which encodes an amino acid sequence of a protein capable of hydrolyzing a racemic ethyl ester N-benzylazetidine-2-carboxylate asymmetrically and producing an (S)-N-benzylazetidine-2-carboxylic acid predominantly may be selected.

A DNA thus amplified may then be cloned into a vector in accordance with conventional methods such as those described in "Molecular Cloning: A Laboratory Manual 2nd edition" (1989), Cold Spring Harbor Laboratory Press, "Current Protocols in Molecular Biology" (1987), John Wiley & Sons, Inc. ISBNO-471-50338-X and the like. Typically, a plasmid vector included in a TA cloning kit available from Invitogen or a plasmid vector included in a pBluescript II available from Stratagene can for example be used in the cloning.

A DNA of the gene of the present invention may also be obtained by hybridizing a library of chromosomal DNA or a cDNA derived from a microorganism belong to *Aspergillus flavus* with a DNA, as a probe, of about 15 nucleotides or more having a nucleotide sequence encoding the amino acid sequence represented by SEQ ID NO:1 in the conditions described below, followed by detecting a DNA to which such a probe binds specifically.

A method of hybridizing a library of a chromosomal DNA or a cDNA with a probe may be a colony hybridization or a plaque hybridization, and it depends on the type of the vector used in the preparation of the library. When the library used is constructed using a plasmid vector, a colony hybridization is carried out. Typically, a library DNA is introduced into a host microorganism to obtain a transformant which is then diluted and inoculated onto an agar medium. Then the medium is incubated until a colony appears. When the library is prepared using a phage vector, then a plaque hybridization is performed. Typically, a host microorganism is mixed with a library phage in the conditions allowing an infection to occur and then admixed further with a soft agar medium, which is then inoculated onto an agar medium. Then the medium is incubated until a plaque appears.

In cases of the hybridization described above, a membrane is then mounted on the surface of the agar medium which has been incubated as described above to transfer a transformant or a phage onto the membrane. After treating this membrane with an alkali followed by a neutralization, the DNA is immobilized on the membrane. Typically, in the case of a plaque hybridization, the agar medium described above is covered with a nitrocellulose membrane or a nylon membrane, such as Hybond-N$^{+}$™ (Amersham), and allowed to stand for about 1 minute, thereby allowing a phage particle to be adsorbed onto the membrane. Then the membrane is immersed in an alkaline solution (1.5 M sodium chloride, 0.5 N NaOH) for about 3 minutes to dissolve the phage particle to effect an elution of a phage DNA onto the membrane, followed by a treatment by immersing for about further 5 minutes in a neutralization solution (1.5 M sodium chloride, 0.5 M tris-HCl buffer, pH 7.5). After washing the membrane with a washing solution (0.3 M sodium chloride, 30 mM sodium citrate, 0.2 M tris-HCl buffer, pH 7.5) for about 5 minutes, a baking was performed, for example, at about 80° C. for about 90 minutes to immobilize the phage DNA onto the membrane.

The membrane thus prepared is then subjected to a hybridization using the DNA described above as a probe. The hybridization may for example be performed in accordance with the description in J. Sambrook, E. F. Frisch, T. Maniatis, "Molecular Cloning: A Laboratory Manual 2nd edition (1989)", Cold Spring Harbor Laboratory Press and the like.

A DNA used as a probe may be labeled with a radioactive isotope using a Random Labeling Kit available from Boehringer or TAKARA SHUZO Co., Ltd., and the labeling may also be done by performing a PCR using a probe DNA as a template with using ($\alpha$-$^{32}$P)dCTP instead of a dCTP in a conventional PCR reaction mixture. When a DNA used as a probe is labeled with a fluorescent dye, an ECL Direct Nucleic Acid Labeling and Detection System available from Amersham may for example be used.

While a variation of the reagents and the temperature conditions may be used in a hybridization, a prehybridization solution containing 450 to 900 mM sodium chloride, 45 to 90 mM sodium citrate, together with 0.1 to 1.0% sodium dodecyl sulfate (SDS), 0 to 200 µg/mL modified non-specific DNA, optionally with albumin, ficoll, polyvinylpyrrolidone each at a concentration of 0 to 0.2%, preferably a prehybridization solution containing 900 mM sodium chloride, 90 mM sodium citrate, 1.0% SDS and 100 µg/mL modified calf-thymus DNA is provided in a volume of 50 to 200 µl of per 1 cm$^2$ of a membrane prepared as described above, and the membrane is immersed in this solution over a period of 1 to 4 hours at 42 to 65° C., preferably incubation over 2 hours at 65° C.

Then a hybridization solution containing 450 to 900 mM sodium chloride, 45 to 90 mM sodium citrate, together with 0.1 to 1.0% SDS, 0 to 200 µg/mL modified non-specific DNA, optionally with albumin, ficoll, polyvinylpyrrolidone each at a concentration of 0 to 0.2%, preferably a hybridization solution containing 900 mM sodium chloride, 90 mM sodium citrate, 1.0% SDS and 100 µg/mL modified calf-thymus DNA mixed with the probe prepared as described above (corresponding to $1.0 \times 10^4$ to $2.0 \times 10^6$ cpm per 1 cm of the membrane) is provided in a volume of 50 to 200 µl of per 1 cm$^2$ of a membrane, and the membrane is immersed in this solution over a period of 12 to 20 hours at 42 to 65° C., preferably incubation over 16 hours at 65° C., thereby performing a hybridization.

After this hybridization, the membrane is taken out and washed for 15 minutes twice with a solution containing 15 to 300 mM sodium chloride, 1.5 to 30 mM sodium citrate and 0.1 to 1.0% SDS at 42 to 65° C., preferably with a solution containing 15 mM sodium chloride, 1.5 mM sodium citrate and 1.0% SDS at 65° C. Thereafter, the membrane is rinsed gently with 2×SSC solution (300 mM sodium chloride, 30 mM sodium citrate) and then dried.

This membrane is subjected, for example, to an autoradiography to detect the location of the probe on the membrane, whereby detecting where the DNA which hybridizes with the probe used is located on the membrane. A clone corresponding to the location of the detected DNA on the membrane is identified on the agar medium used initially, and is picked up to isolate the clone having the relevant DNA.

A DNA obtained as described above may be cloned to a vector in accordance with conventional methods such as those described in "Molecular Cloning: A Laboratory Manual 2nd edition" (1989), Cold Spring Harbor Laboratory Press, "Current Protocols in Molecular Biology" (1987), John Wiley & Sons, Inc. ISBNO-471-50338-X and the like. A vector which may be utilized may for example be pUC119 (TAKARA SHUZO Co., Ltd.), pTV118N (TAKARA SHUZO Co., Ltd.), pBluescriptII (Toyobo Co., Ltd.), pCR2.1-TOPO (Invitrogen), pTrc99A (Pharmacia), pKK331-1 (Pharmacia) and the like.

The nucleotide sequence of the DNA described above may for example be sequenced by a dideoxy terminator method described by F. Sanger, S. Nicklen and A. R. Coulson in "Proceeding of Natural Academy of Science, USA (1977)", 74:p5463–5467 and the like. A sample for sequencing of the nucleotide may be prepared also using a commercial reagent such as ABI PRISM Dye Terminator Cycle Sequencing Ready Reaction Kit available from Perkin Elmer.

A protein encoded by a DNA described above may be checked for its ability of hydrolyzing the cyclic imino acid ester (1) stereoselectively by a method exemplified below. For example, the relevant DNA is inserted into a vector as being attached downstream of the promoter capable of functioning in a host cell, and the vector is introduced into the host cell to obtain a transformant. Then, a culture of the transformant is reacted with a compound described above to yield a reaction product, which is then analyzed. A transformant having an ability of producing the (S)-cyclic imino acid (2) predominantly, has a DNA of the gene of the present invention which encodes a protein having such ability.

In a nucleotide sequence in a DNA of the gene of the present invention which encodes a protein, especially an N-terminal region thereof, having an ability of hydrolyzing the cyclic imino acid ester (1) asymmetrically and producing the (S)-cyclic imino acid (2) predominantly, a substitution of a codon encoding an amino acid used with a codon used more frequently in a host cell may be useful to increase the expression efficiency of this protein in the host cell. In this context, "an N-terminal region" means a region consisting of about 10 to about 50 amino acid residues including the N-terminal of the protein.

In order to increase the expression efficiency in a host cell, a method using a DNA encoding the N-terminal of a known protein capable of being used in such a host cell may also be useful.

A DNA having a nucleotide sequence formed by binding a nucleotide sequence encoding the amino acid sequence represented by SEQ ID NO:1 or a part thereof to the downstream of a nucleotide sequence encoding an amino acid sequence in the N-terminal region of a protein derived from a host cell, for example, an amino acid sequence in the N-terminal region of a β-galactosidase of *E. coli* in a case where the host cell is *E. coli*, with their reading frames being matched with each other, is prepared and the resultant DNA may be utilized as the gene of the present invention or its substitute. Those exemplified more specifically are a DNA having a nucleotide sequence formed by binding a nucleotide sequence encoding the amino acid sequence represented by SEQ ID NO:1 to the downstream of a nucleotide sequence encoding an amino acid sequence from the N-terminal residue to the 25th amino acid residue of an *E.coli*-derived β-galactosidase, a DNA having a nucleotide sequence formed by binding a nucleotide sequence encoding the amino acid sequence represented by Amino Acid No.35 to 255 in the amino acid sequence represented by SEQ ID NO:1 to the downstream of a nucleotide sequence encoding an amino acid sequence from the N-terminal residue to the 25th amino acid residue of an *E. coli*-derived β-galactosidase, and the like.

The gene of the present invention may comprise a nucleotide sequence encoding an amino acid sequence capable of functioning as a secretion signal in a host cell. An amino acid sequence capable of functioning as a secretion signal in a host cell may for example be an amino acid sequence of a signal peptide derived from a protein which is secreted usually in the host cell. Specifically, an amino acid sequence capable of functioning as a secretion signal in *E. coli* may for example be an amino acid sequence of a signal peptide of a membrane-localized protein such as a lipoprotein (Lpp), an amino acid sequence of a signal peptide of a periplasm localized protein such as an alkaline phosphatase (phoA) and a maltose-binding protein (MalE) and the amino acid sequence represented by SEQ ID NO:3, while an amino acid sequence capable of functioning as a secretion signal in a microorganism of Bacillus may for example be an amino acid sequence of a signal peptide of a protein such as an α-amylase (BLA) and a protease inhibitor (BbpPI) (BIOCHEMICAL EXPERIMENT 37 "Protein secretion and intracellular transportation", S. Mizushima, GAKKAISH-UPPAN Center, Proteins, nucleic acids and enzymes, a special issue, "Advancement in Protein engineering; For designing proteins", KYORITSU SHUPPAN).

In order to express the gene of the present invention in a host cell, a gene formed by binding a promoter capable of functioning in the host cell to the gene of the present invention in a functional form is introduced into the host cell. The term "in a functional form" referred herein means the condition in which the gene of the present invention is bound to a promoter in a manner enabling an expression under the regulation by the promoter when such gene has been transduced into a host cell and had transformed the host cell. Such promoter may for example be a promoter of the lactose operon of *E. coli,* a promoter of the tryptophan operon of *E. coli,* or a synthetic promoter capable of functioning in an *E. coli* cell such as tac promoter or trc promoter. An original promoter of the gene of the present invention may also be used.

In general, the gene of the present invention which is bound in a functional form to a promoter capable of functioning in a host cell is inserted in a vector such as those described above, which is then introduced into a host cell. Such vector may for example be a vector containing a selective marker gene (e.g., antibiotic resistant gene such as kanamycin resistant gene, neomycin resistant gene) for the purpose of selecting a transformant into which the vector of the present invention is introduced based on a phenotype of such selective marker gene.

A host cell into which the gene of the present invention is introduced may for example be a cell of a microorganism belonging to Escherichia, Bacillus, Corynebacterium, Staphylococcus, Streptomyces, Saccharomyces, Kluyveromyces, Aspergillus and the like. A method for introducing a gene into a host cell may be any one of those selected usually depending on the host cells, and may be a calcium chloride method described in "Molecular Cloning: A Laboratory Manual 2nd edition" (1989), Cold Spring Harbor Laboratory Press, "Current Protocols in Molecular Biology" (1987), John Wiley & Sons, Inc. ISBNO-471-50338-X or an electroporation described in "Methods in Electroporation: Gene Pulser/*E.coli* Pulser System", Bio-Rad Laboratories, (1993).

A transformant into which the gene of the present invention is introduced may be selected based on a phenotype of a selective marker gene contained in a vector described above. To ensure that a transformant has the gene of the present invention, a vector DNA is prepared from the transformant and subjected to conventional methods such as those described in "Molecular Cloning" (J. Sambrook et al., Cold Spring Harbor, 1989) (restriction enzyme site identification, nucleotide sequencing, southern hybridization, and the like).

The protein of the present invention may for example be produced by cultivating a microorganism having the gene of the present invention. A medium in which such microorganism is cultivated may be any one of those used usually for growing a microorganism which contains a carbon source and a nitrogen source, organic and inorganic salts as appropriate. A carbon source may for example be a saccharide such as glucose, dextrin, sucrose, a sugar alcohol such as glycerol, an organic acid such as fumaric acid, citric acid and pyruvic acid, as well as an animal fat, a plant oil and a molasses. The amount of a carbon source listed above to be added to a medium is usually about 0.1% to 20% (w/v) based on the total amount of the medium.

A nitrogen source may for example be a naturally-occurring organic nitrogen source such as a meat extract, peptone, an yeast extract, a malt extract, a soybean powder, a corn steep liquor, a cottonseed powder, a dried yeast and a casamino acid, or amino acids, an ammonium salt or a nitrate salt of an inorganic acid such as sodium nitrate, ammonium chloride, ammonium sulfate and ammonium phosphate, an ammonium salt of an organic acid such as ammonium fumarate and ammonium citrate, as well as other inorganic and organic nitrogen source such as urea. Among those listed above, an ammonium salt of an organic acid, a naturally-occurring organic nitrogen source and amino acids may mostly be used also as a carbon source. The amount of a nitrogen source to be added is usually about 0.1 to 30% (w/v) based on the total amount of the medium.

An organic or inorganic salt may for example be chlorides, sulfates, acetates, carbonates and phosphates of potassium, sodium, magnesium, iron, manganese, cobalt and zinc, and those exemplified typically are sodium chloride, potassium chloride, magnesium sulfate, ferrous sulfate, manganese sulfate, cobalt chloride, zinc sulfate, copper sulfate, sodium acetate, calcium carbonate, sodium carbonate, monopotassium hydrogen phosphate and dipotassium hydrogen phosphate, which may usually be added in an amount of about 0.0001 to 5% (w/v) based on the total amount of the medium. In a case of a host cell into which a gene formed by binding the gene of the present invention to an allolactose-induced promoter, such as tac promoter, trc promoter, lac promoter and the like is introduced in a functional form, an agent to induce the production of the protein of the present invention, such as isopropyl thio-β-D-galactoside (IPTG), may be added to a medium.

A cultivation may be carried out in accordance with a method used usually to grow a microorganism, including a liquid phase cultivation such as a test tube shaking cultivation, a reciprocal shaking cultivation, jar fermenter cultivation and a tank cultivation, or a solid phase cultivation. When a jar fermenter is used, an aseptic air should be introduced into the jar fermenter usually at an aeration rate of about 0.1 to about 2 times of that of the culture fluid volume per minute. The temperature at which the cultivation is performed may vary within the range allowing a microorganism to be grown, and preferably ranges from about 15° C. to about 40° C., and the pH of the medium preferably ranges from about 6 to about 8. The cultivation time may vary depending on the cultivation conditions, and is preferably about 1 day to about 5 days.

The protein of the present invention encompasses a protein comprising any of the following amino acid sequences:

(i) the amino acid sequence represented by SEQ ID NO:1;

(ii) an amino acid sequence corresponding to the nucleotide sequence represented by SEQ ID NO:2;

(iii) an amino acid sequence of a protein which is capable of hydrolyzing a racemic ethyl N-benzylazetidine-2-carboxylate asymmetrically and producing an (S)-N-benzylazetidine-2-carboxylic acid predominantly and which consists of a part of the amino acid sequence represented by SEQ ID NO:1;

(More specifically, for example, an amino acid sequence represented by Amino Acid No.35 to 255 in the amino acid sequence represented by SEQ ID NO:1; an amino acid sequence represented by Amino Acid No.79 to 255 in the amino acid sequence represented by SEQ ID NO:1; an amino acid sequence corresponding to the nucleotide sequence represented by Nucleotide No.103 to 765 in the nucleotide sequence represented by SEQ ID NO:2; an amino acid sequence corresponding to the nucleotide sequence represented by Nucleotide No.235 to 765 in the nucleotide sequence represented by SEQ ID NO:2)

(iv) an amino acid sequence of a protein which is capable of hydrolyzing a racemic ethyl N-benzylazetidine-2-carboxylate asymmetrically and producing an (S)-N-benzylazetidine-2-carboxylic acid predominantly and which is encoded by a nucleotide sequence which hybridizes under a stringent condition with a DNA consisting of a nucleotide sequence encoding the amino acid sequence represented by SEQ ID NO:1;

(v) an amino acid sequence of a protein which is capable of hydrolyzing a racemic ethyl N-benzylazetidine-2-carboxylate asymmetrically and producing an (S)-N-benzylazetidine-2-carboxylic acid predominantly and which has a molecular weight of about 25,000 daltons determined by an SDS-PAGE; and, (vi) an amino acid sequence of a protein which is capable of hydrolyzing a racemic ethyl N-benzylazetidine-2-carboxylate asymmetrically and producing an (S)-N-benzylazetidine-2-carboxylic acid predominantly and which has an amino acid homology of 60% or higher with the amino acid sequence represented by SEQ ID NO:1; and the like.

A method for purifying the protein of the present invention from a culture of a microorganism having the gene of the present invention may be an conventional method used in purification of protein such as those exemplified below.

First, cells are collected from a culture broth of a microorganism by centrifugation or the like, and then destroyed physically by an ultrasonic treatment, a DYNO-MILL treatment or a french press treatment or chemically by a surfactant or a cell-lyzing enzyme such as lysozyme. From the resultant thus obtained, an insoluble material is removed using centrifugation or membrane filteration, etc., to prepare a cell-free extract, which is then fractionated by any appropriate means for separation and purification, such as cation exchange chromatography, anion exchange chromatography, hydrophobic chromatography, gel chromatography and the like, thereby purifying the esterase of the present invention. A support used in chromatography may for example be a resin support such as cellulose, dextran and agarose modified with a carboxymethyl (CM) group, a DEAE group, a phenyl group or a butyl group. A commercially available column already packed with any support such as Q-Sepharose FF, Phenyl-Sepharose HP (Trade Name, Amersham Pharmacia Biotech), TSK-gel G3000SW (Trade Name, Tosoh Corporation) may also be used.

A procedure for purifying the protein of the present invention is exemplified below.

Cells of a microorganism producing the protein of the present invention are collected by centrifugation, and then suspended in a buffer such as 20 mM potassium phosphate (pH 7.0). The suspension is treated using a DYNO-MILL or the like, and the resultant thus obtained is centrifuged at about 10000×g for about 15 minutes to obtain a supernatant, which is then filtered through a membrane filter to remove insolubles to obtain a cell-free extract. The cell-free extract thus obtained is then loaded, for example, onto a Q-Sepharose FF column or a Q-Sepharose HP column (Trade Name, Amersham Pharmacia Biotech) and the column is eluted with a linear gradient of sodium chloride to obtain a series of fractions. A fraction containing the protein of the present invention is then loaded, for example, onto a Phenyl-Sepharose HP column (Trade Name, Amersham Pharmacia Biotech) and the column is eluted with a linear gradient of ammonium sulfate to obtain a series of fractions. A fraction containing the protein of the present invention is concentrated using ultrafiltration membrane or the like, and then loaded, for example, onto a TSK-gel G3000 SW column (600 mm×7.5 mm ID) (Trade Name, Tosoh Corporation) and eluted, for example, with a 50 mM sodium phosphate containing 0.15 M sodium chloride to obtain fractions, whereby purifying the protein of the present invention. A fraction containing the protein of the present invention may for example be selected based on the ability of hydrolyzing a racemic ethyl N-benzylazetidine-2-carboxylic acid asymmetrically and producing an (S)-N-benzylazetidine-2-carboxylic acid predominantly.

An ester asymmetric hydrolysis by the protein of the present invention, or a microorganism having the protein of the present invention or a treated product thereof may for example be a reaction in which the cyclic imino acid ester (1) is hydrolyzed asymmetrically to produce an (S)-cyclic imino acid, preferably a reaction in which a compound of the cyclic imino acid ester (1) wherein $R^1$ is an alkyl group having 1 to 8 carbon atoms in which one or more hydrogen atoms may optionally be substituted with a halogen atom or a nitro group is hydrolyzed asymmetrically to produce an (S)-cyclic imino acid corresponding to the compound described above, or a reaction in which a compound of the cyclic imino acid ester (1) wherein $R^2$ is (a) an aralkyl group having 7 to 19 carbon atoms in which one or more hydrogen atoms bound to its aromatic ring may optionally be substituted with an alkyl group having 1 to 8 carbon atoms, an alkoxy group having 1 to 8 carbon atoms, a halogen atom and a nitro group or (b) an alkyloxycarbonyl group having 2 to 9 carbon atoms in which one or more hydrogen atoms may optionally be substituted with an alkoxy group having 1 to 8 carbon atoms, a halogen atom or a nitro group is hydrolyzed asymmetrically to produce an (S)-cyclic imino acid corresponding to the compound described above.

A method for producing an (S)-cyclic imino acid in accordance with the present invention is explained below. The cyclic imino acid ester (1) is brought into contact with the protein of the present invention or a microorganism containing the gene of the present invention or a treated product thereof to yield an (S)-cyclic imino acid.

In the cyclic imino acid ester (1), $R^2$ is a protective group for an N in an azetidine ring or a pyrrolidine ring, such as, for example, an aralkyl group having 7 to 19 carbon atoms; an acyl group having 2 to 13 carbon atoms such as an alkylcarbonyl group having 2 to 5 carbon atoms, an arylcarbonyl group having 7 to 13 carbon atoms and the like; an alkyloxycarbonyl group having 2 to 9 carbon atoms; an aralkyloxycarbonyl group having 8 to 10 carbon atoms; an alkenyloxycarbonyl group having 3 to 9 carbon atoms; an aryloxycarbonyl group having 7 to 13 carbon atoms; an alkyl group having 1 to 8 carbon atoms; an alkenyl group having 2 of 8 carbon atoms; an aryl group having 6 to 12 carbon atoms; an arylsulfonyl group having 6 to 12 carbon atoms and the like.

In an aralkyl, arylcarbonyl, aralkyloxycarbonyl, aryloxycarbonyl, aryl or arylsulfonyl group described above, one or more, usually 1 to 5, hydrogen atoms bound to the aromatic ring may optionally be substituted with at least one selected from an alkyl group having 1 to 8 carbon atoms, an alkoxy group having 1 to 8 carbon atoms, a halogen atom and a nitro group. In an alkylcarbonyl, alkyloxycarbonyl or alkyl group described above, one or more, usually 1 to 3, hydrogen atoms may optionally be substituted with at least one selected from an alkoxy group having 1 to 8 carbon atoms, a halogen atom and a nitro group.

Such aralkyl group may for example be benzyl, p-chlorobenzyl, α-phenylethyl, β-phenylethyl, phenylpropyl, benzhydryl and triphenylmethyl groups; an alkylcarbonyl group may for example be acetyl, chloroacetyl and trifluoroacetyl groups; an arylcarbonyl group may for example be benzoyl and p-phenylbenzoyl group; an alkyloxycarbonyl group may for example be t-butoxycarbonyl and trichloroethyloxycarbonyl groups; an aralkyloxycarbonyl group may for example be benzyloxycarbonyl, p-nitrobenzyloxycarbonyl and 2-phenylethyloxycarbonyl groups; an alkenyloxycarbonyl group may for example be an allyloxycarbonyl group; an aryloxycarbonyl group may for example be a 2,4,6-tri-t-butylphenyloxycarbonyl group; an alkyl group may for example be methyl, ethyl, n-propyl, isopropyl, n-butyl, isobutyl, sec-butyl and t-butyl groups; an alkenyl group may for example be an allyl group; an aryl group may for example be a phenyl group; an arylsulfonyl group may for example be p-toluenesulfonyl, benzenesulfonyl, p-methoxybenzenesulfonyl and m-nitrobenzenesulfonyl groups. These aralkyl groups are exemplified preferably, and those exemplified more preferably are benzyl, p-chlorobenzyl, α-phenylethyl, benzhydryl and triphenylmethyl group, and those preferred particularly are benzyl, p-chlorobenzyl and α-phenylethyl groups.

The cyclic imino acid ester (1) may have an asymmetric carbon atom other than the carbon atom on the 2-position as in the case, for example, where $R^2$ is an α-alkyl-substituted aralkyl group such as α-phenylethyl group. Typically, when $R^2$ is an α-phenylethyl group, those which may be contemplated are methyl N-[(S)-phenylethyl]-azetidine-2-carboxylate, methyl N-[(R)-phenylethyl]-azetidine-2-carboxylate and a mixture thereof, or methyl N-[(S)-phenylethyl]-pyrrolidine-2-carboxylate, methyl N-[(R)-phenylethyl]-pyrrolidine-2-carboxylate and a mixture thereof.

$R^1$ may for example be an alkyl group having 1 to 8 carbon atoms, an aralkyl group having 7 to 19 carbon atoms, an alkenyl group having 2 to 5 carbon atoms and an aryl group having 6 to 12 carbon atoms. In an aralkyl or aryl group described above, one or more, usually 1 to 5, hydrogen atoms bound to the aromatic ring may optionally be substituted with at least one selected from an alkyl group having 1 to 8 carbon atoms, an alkoxy group having 1 to 8 carbon atoms, a halogen atom or a nitro group, and, in an alkyl group described above, one or more, usually 1 to 3, hydrogen atoms may optionally be substituted with at least one selected from an alkoxy group having 1 to 8 carbon atoms, a halogen atom or a nitro group.

Such alkyl group may for example be methyl, ethyl, n-propyl, isopropyl, n-butyl, isobutyl, sec-butyl and t-butyl groups; an aralkyl group may for example be benzyl, p-chlorobenzyl, α-phenylethyl, β-phenylethyl, phenylpropyl, benzhydryl and triphenylmethyl groups; an alkenyl group may for example be an allyl group; an aryl group may for example be a phenyl group. These alkyl groups are exemplified preferably, and those exemplified more preferably are lower alkyl groups (having 1 to 4 carbon atoms).

Typically, the cyclic imino acid ester (1) may for example be methyl N-benzylazetidine-2-carboxylate, methyl N-p-chlorobenzylazetidine-2-carboxylate, methyl N-[(S)-phenylethyl]-azetidine-2-carboxylate, methyl N-[(R)-phenylethyl]-azetidine-2-carboxylate, methyl N-β-phenylethylazetidine-2-carboxylate, methyl N-phenylpropylazetidine-2-carboxylate, methyl N-benzhydrylazetidine-2-carboxylate, methyl N-triphenylmethylazetidine-2-carboxylate, methyl N-acetylazetidine-2-carboxylate, methyl N-chloroacetylazetidine-2-carboxylate, methyl N-trifluoroacetylazetidine-2-carboxylate, methyl N-benzoylazetidine-2-carboxylate, methyl N-p-phenylbenzoylazetidine-2-carboxylate, methyl N-t-butoxycarbonylazetidine-2-carboxylate, methyl N-trichloroethyloxycarbonylazetidine-2-carboxylate, methyl N-benzyloxycarbonylazetidine-2-carboxylate, methyl N-p-nitrobenzyloxycarbonylazetidine-2-carboxylate, methyl N-2-phenylethyloxycarbonylazetidine-2-carboxylate, methyl N-allyloxycarbonylazetidine-2-carboxylate, methyl N-2,4,6-tri-t-butylphenyloxycarbonylazetidine-2-carboxylate, methyl N-methylazetidine-2-carboxylate, methyl N-ethylazetidine-2-carboxylate, methyl N-n-propylazetidine-2-carboxylate, methyl N-isopropylazetidine-2-carboxylate, methyl N-n-butylazetidine-2-carboxylate, methyl N-isobutylazetidine-2-carboxylate, methyl N-sec-butylazetidine-2-carboxylate, methyl N-t-butylazetidine-2-carboxylate, methyl N-allylazetidine-2-carboxylate, methyl N-phenylazetidine-2-carboxylate, methyl N-p-toluenesulfonylazetidine-2-carboxylate, methyl N-benzenesulfonylazetidine-2-carboxylate, methyl N-methoxybenzenesulfonylazetidine-2-carboxylate and methyl N-nitrobenzenesulfonylazetidine-2-carboxylate, as well as those compounds in which the azetidine rings in the compounds listed above are replaced with pyrrolidine rings. Those also exemplified are those compounds in which the methylesters in the compounds listed above are replaced for example with ethylester, n-propylester, isopropylester, n-butylester, isobutylester, sec-butylester, t-butylester, benzylester, (S)-α-phenylethylester, (R)-α-phenylethylester, β-phenylethylester, phenylpropylester, benzhydrylester, triphenylmethylester, allylester, phenylester and naphthylester.

The method described above is performed usually in the presence of water. Such water may exist in various forms such as water and an aqueous buffer solution. Such aqueous buffer solution may for example be an aqueous buffer solution of an inorganic acid salt and an aqueous buffer solution of an organic acid salt, and such aqueous buffer solution of an inorganic acid salt may for example be an aqueous solution of a phosphate of an alkaline metal such as an aqueous solution of sodium phosphate and an aqueous solution of potassium phosphate, and aqueous buffer solution of an organic acid salt may for example be an aqueous solution of an acetate of an alkaline metal such as an aqueous solution of sodium acetate and an aqueous solution of potassium acetate. The amount of water is 0.5 parts by mole or more based on the cyclic imino acid ester (1), and any one of various forms of waters described above may be used as a solvent. When an aqueous buffer solution is used as a solvent, it is used usually in an amount of 100 parts by weight or less based on the cyclic imino acid ester (1).

Also in the method described above, an organic solvent such as a hydrophobic organic solvent and a hydrophilic organic solvent may also be present in addition to various forms of waters described above.

Such hydrophobic organic solvent may for example be an ether such as t-butylmethylether and isopropylether and a hydrocarbon such as toluene, hexane, cyclohexane, heptane and isooctane, while a hydrophilic organic solvent may for example be an alcohol such as t-butanol, methanol, ethanol, isopropanol and n-butanol, an ether such as tetrahydrofuran, a sulfoxide such as dimethylsulfoxide, a ketone such as acetone and a nitrile such as acetonitrile. Each of these hydrophobic and hydrophilic solvents may be used as a sole solvent or in combination with each other, and a combination of a hydrophobic solvent and a hydrophilic solvent may also be contemplated.

When such an organic solvent is used, it is used in an amount usually of 100 parts by weight or less, preferably 0.1 to 50 parts by weight based on the cyclic imino acid ester (1).

The method described above is performed, for example, by mixing a water or an aqueous buffer solution, the cyclic imino acid ester (1) and the protein of the present invention or a microorganism having the gene of the present invention or a treated product thereof, optionally with an organic solvent, with stirring or shaking.

The pH at which the reaction in the method described above proceeds may appropriately be selected, and usually pH 4 to 10.

The reaction temperature is preferably 0° C. to 70° C. in view of the stability and the reaction rate, more preferably 10° C. to 40° C.

The amount of the protein of the present invention or a microorganism having the gene of the present invention or a treated product thereof may appropriately be selected taking the reaction rate and the selectivity into consideration, and usually 0.001 to 50 parts by weight, preferably 0.002 to 20 parts by weight based on the cyclic imino acid ester (1).

The endpoint of the reaction may for example be determined by monitoring the reaction rate of the cyclic imino acid ester (1) in a reaction mixture by liquid chromatography or the like. For a preferable selectivity, the reaction is terminated before the conversion rate of the cyclic imino acid ester (1) exceeds 50%. The reaction time is usually about 5 minutes to about 4 days.

The (S)-cyclic imino acid (2) may be recovered from a reaction mixture by known conventional methods. For example, a reaction mixture is extracted with an organic solvent such as hexane, heptane, t-butylmethylether, ethyl acetate and toluene and the organic phase is separated off to obtain an aqueous phase. The aqueous layer thus obtained is subjected to ion exchange chromatography or the like to separate the salts off and then concentrated and purified, if necessary, by column chromatography.

The protein of the present invention or a microorganism having the gene of the present invention or a treated product thereof may be used as a biocatalyst in various forms.

Typically, such forms include a culture of a microorganism having the gene of the present invention, cells of a microorganism having the gene of the present invention, a treated product thereof, a cell-free extract, a crude protein, a purified protein and the like. A treated product thereof may for example be lyophilized cells, organic solvent-treated cells, dried cells, milled cells, autolysate of cells, sonicated treated cells, a cell free extract, alkali-treated cells, and immobilized catalysts obtained by a known method such as a support binding method using an adsorption onto an inorganic support such as a silica gel or a ceramic, a cellulose or an ion exchange resin, as well as an inclusion method using an enclosure in a polymeric matrix such as a polyacrylamide gel, a sulfur-containing polysaccharide gel (e.g., carrageenin gel), an alginic acid gel or an agar gel may also be used.

In view especially of industrial production employing a microorganism having the gene of the present invention, a treated product which is obtained by sterilizing a cell is used more preferably rather than a viable cell since it poses a less limitation of production facility. A method for sterilizing a cell may for example be a physical sterilization (heating (drying, moistened heating), freezing, light, sonication, filtration, electric treatment) or a method using a chemical (alkali, acid (organic and inorganic), halogen, oxidant, sulfur, boric acid, arsenic, metal, alcohol, phenol, amine, sulfide, ether, aldehyde, ketone, cyanide or compounds thereof, as well as antibiotic), which may be combined if necessary. Among these treatments, treatment methods which result in less inactivation of enzyme and which reduce the adverse effects on the enzymatic reaction system, such as a residual chemical or a contamination, is generally preferred. For example, a gene recombinant culture is adjusted at pH 8 to pH 12 with NaOH or $Na_2CO_3$ and kept at 0° C. to 60° C., preferably stirred at pH 9.0 to pH 10.5 at a temperature of 10° C. to 30° C. for 10 minutes to 60 hours, thereby effecting sterilization by an alkaline treatment. The culture thus sterilized may also be used as an immobilized material.

EXAMPLES

The present invention is further described in the following examples, which are not intended to restrict the invention.

Example 1

(cDNA Library Preparation)

Two hundred mL of a medium (10 g/L glucose, 7 g/L polypeptone, 5 g/L yeast extract, 5 g/L $K_2HPO_4$, pH 7.2) was placed in a 500 mL flask and sterilized at 121° C. for 15 minutes. This medium was inoculated with a culture of *Aspergillus flavus* strain ATCC11492 which had previously been grown in the same medium at 30° C. for 48 hours with shaking, and then cultivated at 30° C. for 72 hours with shaking. After cultivating, cell were collected by centrifugation (8,000×g, 10 minutes), and a resultant cell pellet (2 to 5 mm in radius) was washed three times with a 20 mM potassium phosphate buffer solution (pH7.0). Washed cells were frozen at −80° C.

40 g of the frozen cells obtained as described above were subjected to a phenol-chloroform-isoamylalcohol extraction method to obtain about 12.6 mg (OD260/OD280=2.0) of total RNA. Then 1 mg of the total RNA and was applied to an Oligotex (dT) 30-Super column (TAKARA SHUZO) and 7.6 μg (OD260/OD280=1.75) of RNA having a poly(A) was prepared.

A cDNA library was prepared by the method described in "BIOLOGY GENERAL CATALOG, 1997/98, Vol.1, Gene Engineering, E-24 to 27". First, 2.8 μg of the RNA having a poly(A), Oligo(dT)18-linker primer ((GA)10ACGCGTCGACTCGAGCGGCCGCGGACCG(T)18 (TAKARA SHUZO), RAV-2 Reverse Transcriptase (TAKARA SHUZO) and SuperScriptII Reverse Transcriptase (GIBCO BRL) were used to synthesize single-stranded cDNA.

After the single-stranded cDNA synthesis reaction, the reaction mixture was brought into contact with E. coli DNA polymerase (TAKARA), E. coli RNase/E. coli DNA Ligase mixture (TAKARA SHUZO) and T4 DNA polymerase (TAKARA SHUZO) to synthesize a double-stranded cDNA and to obtain a blunt end. Then a ligation with an SalI adapter (GIBCO BRL) was conducted. Then DNA obtained by the ligation was digested with NotI and subjected to a spin column Spin-OUT™ Column GT-1200 (TAKARA SHUZO) to remove a low molecular weight DNA and ligated with a λ ZipLox [SalI-NotI arm] (GIBCO BRL). The DNA obtained by the ligation was then packaged using an in vitro packaging kit (STRATAGENE).

Example 2

(1) Esterase Purification

About 120 g of −80° C.-frozen cells of *Aspergillus flavus* strain ATCC11492 which had been prepared in a procedure similar to that in Example 1 was suspended in a 50 mM potassium phosphate buffer solution (pH 7.0) containing 0.05% Tween 80 and milled using DYNO-MILL (WILLY A. BACHOFEN AG) Glass beads, 0.1 to 0.2 mmφ, 3000 rpm, 30 minutes). The resultant thus obtained was centrifuged (10,000×g, 10 minutes) to obtain a supernatant, which was further ultracentrifuged (100,000×g, 120 minutes) to obtain 200 mL of the supernatant.

200 mL of the supernatant thus obtained was loaded onto a Q-Sepharose HP XK 16/10 column (Amersham Pharmacia Biotech) equilibrated with a BIS-TRIS buffer (20 mM bis-trispropane buffer containing 0.05% Tween 80, pH 7.0) and then washed with the BIS-TRIS buffer. After washing, proteins were eluted with a gradient of 0 to 0.7 M NaCl in 140 mL of a BIS-TRIS buffer to obtain 48 mL of an eluted fraction (active fraction) having an esterase activity described below (hereinafter referred to as the present esterase activity).

The esterase activity was assayed as follows. 0.02 g of a racemic ethyl N-benzylazetidine-2-carboxylate, 1.0 mL of t-butylmethylether (MTBE) and 3.5 mL of 100 mM potassium phosphate buffer (pH 7.0) were placed in a 10 mL screw-capped tube and kept at 35° C. for 15 minutes and then supplemented with about 200 μl of the eluted fraction and then shaken reciprocally (120 str/min) at 35° C. for 60 minutes, thereby performing a reaction. 400 μL of this reaction mixture was combined with 1 mL of MTBE and stirred and then centrifuged (12,000 rpm, 5 minutes) to fractionate 200 μl of an aqueous phase. This aqueous phase was subjected to a 5 to 20-fold dilution with a mobile phase for HPLC (20 mM $KH_2PO_4$ (pH3.8):acetonitrile=90:10) and filtrated through a 0.2 μm filter to separate a microparticle off and then subjected to HPLC under the condition described below to quantify N-benzylazetidine-2-carboxylic acid.

Quantification of N-benzylazetidine-2-carboxylate
Column: ODS-A212 (SUMIKA BUNSEKI CENTER)
Mobile phase: 20 mM $KH_2PO_4$:acetonitrile=90:10
Flow rate: 1 mL/min
Temperature: 40° C.
Detection wavelength: 220 nm The optical isomers of the N-benzylazetidine-2-carboxylate produced were analyzed as follows. 1 mL of the reaction mixture was combined with 400 μL of MTBE and stirred and then centrifuged (12,000 rpm, 5 minutes) to obtain 200 μl of an aqueous phase which was then lyophilized for 12 hours. A residue was combined with 100 μl of acetonitrile and centrifuged (12,000 rpm, 5 minutes) to separate an insoluble off to obtain 50 μl of an acetonitrile phase, which was combined with 200 μl of a mobile phase for HPLC for an optical isomer analysis (2 mM copper sulfate:acetonitrile=90:10) and filtrated through a 0.2 μl filter to obtain a sample for the optical isomer analysis. The condition of HPLC for the optical isomer analysis was described below.

Optical Isomer Analysis of N-benzylazetidine-2-carboxylate
Column: SUMICHIRAL OA-6000 (SUMIKA BUNSEKI CENTER)
Mobile phase: 2 mM Copper sulfate:acetonitrile=90:10
Flow rate: 1 mL/min
Temperature: 35° C.
Detection wavelength: 254 nm The N-benzylazetidine-2-carboxylic acid produced as a result of a spontaneous hydrolysis, using a procedure similar to that described above except that no eluted fraction was added, was also produced and was also quantified.

1 [U] of the esterase thus determined was defined as the amount of the enzyme which produced 1 nmol of N-benzylazetidine-2-carboxylic acid per 1 minute. Thus:

1 [U]=[N-benzylazetidine-2-carboxylic acid produced in reaction mixture (nmol)−N-benzylazetidine-2-carboxylic acid produced as a result of spontaneous hydrolysis (nmol)]/reaction time (min)

48 mL of the fraction exhibiting the present esterase activity obtained by the column treatment described above was loaded onto a phenyl-Sepharose HP XK 16/10 column (Amersham Pharmacia Biotech) equilibrated with a BIS-TRIS buffer containing 0.7 M ammonium sulfate and then washed with the buffer solution having a composition similar to that of the buffer used for the equilibration. Subsequently, proteins was eluted with a gradient of 0.7 to 0 M ammonium sulfate in 140 mL of a BIS-TRIS buffer, and the present esterase activity was determined as described above, thereby yielding 12 mL of the fraction exhibiting the present esterase activity.

(2) Primer DNA Preparation

The fraction exhibiting the present esterase activity thus obtained was concentrated using CENTRICON 10 (AMICON) and desalted using a desalting column (Fast Desalting Column, Pharmacia) equilibrated with water and then concentrated under reduced pressure. The protein contained in the fraction exhibiting the present esterase activity thus concentrated under reduced pressure was separated by sodium dodecyl sulfate (SDS) polyacrylamide gel electrophoresis (on multigel 10/20 (DAIICH KAGAKU) in an SDS-trisglycine buffer (DAIICH KAGAKU) for electrophoresis at 40 mA for 1.5 hours) in accordance with the method described in Laemmli, U.K., Nature, (1970) 227, 680, and then electro-blotted (20 mA, 120 minutes) on PVDF membrane (Trans-Blot Transfer Medium PVDF Membrane, BIO-RAD) and then stained with Coomassie brilliant blue G250 (BIO-RAD). Based on the comparison of the molecular weight markers and the distances of the development fronts, the band of the stained protein assumed to have a molecular weight of about 25000 daltons was cut and the PVDF membrane containing about 2 pmol of the protein was subjected to a protein sequencer 470 A (Applied Biosystems). As a result, 20 amino acid residues in the direction of the N-terminal were sequenced. The amino acid sequence thus determined is represented by SEQ ID NO:4.

Based on the sequence of the 5th to 10th amino acids of the amino acid sequence thus determined, the mixed oligonucleotide represented by SEQ ID NO: 5 was synthesized. The oligonucleotide was synthesized using DNA autosynthesizer Model 380 A (Applied Biosystems).

Example 3

Using the oligonucleotide represented by SEQ ID NO: 5 and SP6 Promoter Primer (TAKARA SHUZO) as primers and the cDNA library constructed by the method described in Example 1 as a template, PCR was performed (using a Taq polymerase Gold PCR kit produced by Perkin Elmer KIKOTECH). The condition of the PCR are shown below.

| Reaction mixture composition | |
| --- | --- |
| cDNA Library stock solution | 1 µl |
| dNTP (Each 2mM-mix) | 10 µl |
| Primer (5 pmol/µl) | Each 1 µl × 2 |
| 10 × Buffer (with MgCl) | 10 µl |
| Taq Polymerase Gold (2.5 U/µl) | 1 µl |
| Ultrapure water | 76 µl |

PCR Reaction Conditions

A container in which a reaction mixture was charged was set in a GeneAmp PCR System 2400 (PERKIN ELMER) and heated at 98° C. (7 minutes), then subjected to 20 cycles of an incubation at 97° C. (0.3 minutes)-45° C. (1 minute)-72° C. (2 minutes) followed by 20 cycles of an incubation at 94° C. (1 minute)-50° C. (0.3 minutes)-75° C. (2.5 minutes), further followed by a treatment at 70° C. (7 minutes).

A TOPO™TA cloning kit Ver.E (Invitrogen) was used to ligate a gene fragment (about 800 bp) obtained in the PCR described above to a "PCR Product insertion site" which had already been formed in pCR2.1-TOPO vector included in this kit. A ligation mixture thus formed was added to E. coli JM105 competent cells (Pharmacia Biotech) to obtain a transformant introduced with a vector prepared by the ligation. A transformant thus obtained was inoculated to 10 mL of a sterilized LB medium containing 1 mM isopropylthio-β-D-galactoside (IPTG) and 100 µg/mL ampicillin (Ap) (prepared by dissolving one pack of L-broth powder (TAKARA SHUZO) in 100 mL of a distilled water (pH 6.5–6.8) followed by sterilizing at 121° C. for 15 minutes), and cultured in a test tube at 30° C. for 24 hours with shaking. After this cultivation, the mixture was concentrated to a cell density higher by 10 times and the concentrate thus obtained (OD660=about 12) was examined for the present esterase activity by the method described in Example 2 to select a clone of the transformant described above of which the present esterase activity was 0.8 U/OD/mL. A vector possessed by this clone (designated as pYHN1) was prepared using a QIAGEN plasmid kit (QIAGEN) in accordance with the protocol attached to this kit.

Subsequently, the nucleotide sequence of the gene fragment inserted into the pYHN1 was sequenced using a PRISM kit (APPLIED BIOTECHNOLOGY) and an automatic nucleotide sequencer model 373A (APPLIED BIOTECHNOLOGY) together with Genetyx-Mac/ATSQ (SOFTWARE KAIHATSU) and Genetyx-Mac (SOFTWARE KAIHATSU) for analysis. As a result, it was revealed that the gene fragment consisting of the nucleotide sequence of Nucleotide No.103 to 768 in the nucleotide sequence represented by SEQ ID NO:2 is inserted into the pYHN1.

The amino acid sequence (Amino acid No.35 to 48 in SEQ ID NO:1) assumed based on the nucleotide sequence thus revealed was in agreement with the N-terminal amino acid sequence of the protein of the present invention purified from Aspergillus flavus ATCC11492. It was also revealed that a nucleotide sequence encoding 25 amino acid residues after the initiation codon of the lacZα encoded on the vector was attached to the upstream of the gene sequence region from Nucleotide No.103 to 768 in the nucleotide sequence represented by SEQ ID NO: 2 in the pYHN1, with the open reading frame being matched with the nucleotide sequence from Nucleotide No.103 in the nucleotide sequence represented by SEQ ID NO:2.

Example 4

PCR was performed under conditions similar to that in Example 3 using Oligonucleotide RC1 shown in Table 1 and T7 Promoter Primer (TAKARA SHUZO) as primers and the cDNA library described in Example 1 as a template. An amplified fragment (approximately 800 bp) was ligated to a "PCR Product insertion site" in a pCR2.1-TOPO vector attached to a TOPO™TA cloning kit Ver.E. A ligation mixture thus formed was added to E. coli JM105 competent cells (Pharmacia Biotech) to obtain a transformant introduced with a vector prepared by the ligation. A transformant thus obtained was subjected to the procedure similar to that in Example 3 to prepare a vector possessed by this transformant, and the nucleotide sequence of a gene fragment inserted in this vector was analyzed. As a result, it was revealed that the gene fragment consisting of the nucleotide sequence of Nucleotide No.1 to 768 in the nucleotide sequence represented by SEQ ID NO:2 was inserted into this vector.

PCR was performed in the condition similar to that in Example 3 using Oligonucleotide F0 and Oligonucleotide RC1 as primers and the vector described above as a template. An amplified fragment thus obtained (approximately 800 bp) was ligated to a "PCR Product insertion site" in a pCR2.1-TOPO vector in the manner described above, and a resultant plasmid (designated as pYHN0) was used to transducer E. coli JM105 (designated as E. coli JM105/pYHN0). The present esterase activity determined under the conditions described above was 0.047 U/OD/mL. The restriction enzyme map of ORF encoded by pYHN0 is shown in FIG. 1.

TABLE 1

| Oligonucleotide | Nucleotide sequence |
| --- | --- |
| RC1 | AAGCAAGCTTTACAGTGAACATGG |
| F0 | ATGCATCTTCCTATCAAGACCCTCTTT |
| EF8 | ATGGAATTCACTGGTGCCTGCACGGAT |

TABLE 1-continued

| Oligonucleotide | Nucleotide sequence |
|---|---|
| AF1 | CATGAAACAAAGCACTATTGCACTGGCACTCTTACCGTTACT GTTTACCCCTGTGGCAAACG |
| AF2 | CAGCGCCGACCAGCAACCCGGCACAGGAACTGG |
| AR2 | AAACAGTAACGGTAAGAGTGCCAGTGCAATAGTGCTTTGTTT |
| AR3 | AATTCCAGTTCCTGTGCCGGGTTGCTGGTCGGCGCTGCGTTT GCCACAGGGGT |

Example 5

PCR was performed under conditions similar to that in Example 3 using pYHN0 obtained in Example 4 as a template and Oligonucleotide EF8 and Oligonucleotide RC1 shown in Table 1 as primers. An amplified fragment obtained (approximately 800 bp) was inserted into SmaI site of vector pUC18 (TAKARA SHUZO) to prepare a plasmid (designated as pYHN8). The present esterase activity of a transformant obtained by transducing pYHN8 into *E. coli* JM105 was 0.88 U/OD/mL when determined as in to Example 3.

Example 6

A DNA fragment of approximately 800 bp cleaved from pYHN0 by digestion with EcoRI was recovered and inserted into an EcoRI site under the control of trc promoter of vector pTrc99A (Amersham Pharmacia Biotech) to prepare a plasmid (designated as pYHNK1). The present esterase activity of transformants obtained by introducing pYHNK1 into *E. coli* JM105 was 6.7 U/OD/mL when determined as in to Example 3.

Example 7

The present esterase activities of transformants obtained by introducing pYHNK1 into *E. coli* JM109 or an *E. coli* strain DH5α (both being competent cells from TAKARA SHUZO) were 8.48 U/OD/mL or 2.1 U/OD/mL, respectively, when determined by the method as in Example 3.

Example 8

Oligonucleotides AF1, AR2, AF2 and AR3 shown in Table 1 were synthesized. Oligonucleotide AF1 was combined with Oligonucleotide AR2 and Oligonucleotide AF2 was combined with Oligonucleotide AR3, and the combinations were kept at 90° C. for 5 minutes to carry out the respective annealings, and then the annealed combinations were ligated to each other together with pTV118N (TAKARA SHUZO) using a ligation kit (TAKARA SHUZO) to prepare a secretion vector in which a linker was inserted into a NcoI-EcoRI site of pTV118N (the amino acid sequence encoded in the linker region inserted into this secretion vector is represented by SEQ ID NO:3). Into the EcoRI site of this secretion vector, the DNA fragment of approximately 800 bp which was isolated by digestion with EcoRI from pYHN1 which had been obtained in Example 3 was ligated (the resultant plasmid was designated as pYHNK2). The present esterase activity of transformants obtained by introducing this pYHNK2 into *E. coli* strain JM105 (designated as *E. coli* JM105/pYHNK2 strain) was 42.7 U/OD/mL when determined by a method as in Example 2 (except for the reaction time which was 16 minutes in this example).

Example 9

100 mL of a sterilized LB medium containing Ap (50 μg/mL) and IPTG (1 mM) was dispensed into a 500 mL flask, which was inoculated with *E. coli* strain JM105/pYHNK2 which had been grown in a sterilized LB medium containing Ap (50 μg/mL) and was the transformant described in Example 7, and then cultivated at 30° C. for 24 hours with shaking and then centrifuged (6000 rpm, 10 minutes) to collect cells.

The collected cells were suspended in 100 mM potassium phosphate buffer (pH 7.0) to form a cell suspension (cell density OD660=9.2). A 5 mL sample bottle received 0.3 g of a racemic ethyl ester N-benzylazetidine-2-carboxylate, 0.62 g of n-heptane and 1.5 g of a distilled water, followed by 0.5 mL of the cell suspension described above, and the mixture was reacted while stirring (1000 rpm) with a stirrer (1.5 cm) at 30° C. for 30 hours.

The reaction mixture was centrifuged (10,000 rpm, 10 minutes) to obtain an aqueous phase, whose N-benzylazetidine-2-carboxylic acid amount, when determined by the method described in Example 2, was 0.12 g, which corresponded to 43% production (mol/mol) of N-benzylazetidine-2-carboxylic acid based on the racemic ethyl ester N-benzylazetidine-2-carboxylate as a starting material.

When the optical isomers of N-benzylazetidine-2-carboxylic acid were analyzed by the method described in Example 1, the optical purity of N-benzylazetidine-2-carboxylic acid was 98% enantiomer excess of the (S)-(optical isomer ratio [(R)/(S)]=1/99).

Example 11

(1) Preparation of Enzyme Solution

A test tube (18 mm in inner diameter) received 10 mL of a liquid medium (prepared by dissolving 5 g of glycerol, 6 g of a yeast extract, 4 g of monopotassium phosphate and 9.3 g of dipotassium phosphate in 1 L of water and adjusted at pH 7.0 with phosphoric acid) and sterilized and then supplemented with ampicillin at 50 μg/mL. To this mixture, 0.1 mL of the stock solution of the transformant, *E. coli* strain JM105/pYHNK2 described in Example 8, in glycerol, was inoculated and shaken at 30° C. for 12 hours to obtain a preculture. Subsequently, a 3 L compact culture tank (MARUBISHI BIOENGINEER, model MDL) received 1500 mL of a liquid medium (obtained by dissolving 22.5 g of glycerol, 15 g of a yeast extract K2 (Cosmo Shokuhin), 22.5 g of Sogo-amino acid F (Ajinomoto), 6 g of monopotassium phosphate, 3.6 g of magnesium sulfate, 0.06 g of ferrous sulfate heptahydrate and 0.06 g of calcium chloride dihydrate in 1.5 L of water) and sterilized and then adjusted to pH 7.0 with phosphoric acid (4M) and ammonia (14%) using a pH controller attached to the jar fermenter described above. This mixture was supplemented with ampicillin at 50 μg/mL and stirred and then inoculated with 0.75 mL of the preculture and cultivated. The cultivation was performed at 30° C. with the aeration rate of 1 vvm (1.5 L/min) at the shaking rate of 1,000 rpm. 15 hours after initiating the cultivation, IPTG was added at the final concentration of 50

µM, and 28 mL of a sterilized medium (containing 150 g of glycerin, 42 g of Sogo-amino acid F (Ajinomoto) and 28 g of a yeast extract K-2 (Cosmo Shokuhin)) was pumped in (at the pumping rate of 14 mL/hour) and then the cultivation was further continued. After the total cultivation time of 40 hours, a culture broth was obtained.

50 mL of the culture broth thus obtained was centrifuged (6,000 rpm, 10 minutes, 4° C.) to collect the cells, which were then suspended in 30 mL of a hypertonic solution of 100 mM potassium phosphate buffer (pH 7.0). This suspension was then centrifuged again (6,000 rpm, 10 minutes, 4° C.) to recover the cells. The cells thus recovered were re-suspended in 30 mL of sterilized water. This suspension was centrifuged again (6,000 rpm, 10 minutes, 4° C.) to obtain a supernatant. The supernatant thus obtained was lyophilized and the resultant was dissolved in a 100 mM potassium phosphate buffer (pH7.0) to obtain an enzyme solution.

Example 12

40 µl of each of various N-benzyl-L-azetidine carboxylates listed in Table 2, 1.0 mL of methyl-t-butylether and 1.5 mL of 100 mM potassium phosphate buffer (pH7.0) were placed in a 10 mL screw-capped tube and supplemented with 0.5 mL of the enzyme solution prepared in Example 11 (corresponding to 8.8 U) and reacted at 30° C. for 16 hours with shaking. After the reaction, the reaction mixture was centrifuged (12,000 rpm, 5 minutes) to obtain an aqueous phase, whose N-benzylazetidine-2-carboxylic acid amount was determined as described in Example 1. The optical isomers of N-benzylazetidine-2-carboxylic acid were analyzed by the method described in Example 2. The production rate (%) calculated from these results (the production rate (%) of N-benzylazetidine-2-carboxylic acid based on each racemic N-benzylazetidine-2-carboxylate as a starting material) and the optical purity of N-benzylazetidine-2-carboxylic acid are shown in Table 2.

TABLE 2

| Substrate | Production rate (%, mol/mol) | Optical purity of (S)-form (% e.e.) |
|---|---|---|
| Ethyl N-benzylazetidine-2-carboxylate | 43.9 | >98 |
| Methyl N-benzylazetidine-2-carboxylate | 19.5 | >98 |
| Benzyl N-benzylazetidine-2-carboxylate | 2.0 | >98 |
| Propyl N-benzylazetidine-2-carboxylate | 35.7 | >98 |

TABLE 2-continued

| Substrate | Production rate (%, mol/mol) | Optical purity of (S)-form (% e.e.) |
|---|---|---|
| Isopropyl N-benzylazetidine-2-carboxylate | 8.7 | >98 |
| Butyl N-benzylazetidine-2-carboxylate | 28.5 | >98 |

Example 13

40 µL of ethyl N-benzyl-L-pyrrolidine carboxylate, 1.0 mL of methyl-t-butylether and 1.5 mL of 100 mM potassium phosphate buffer (pH 7.0) are placed in a 10 mL screw-capped test tube, and then supplemented with 0.5 mL of the enzyme solution prepared in Example 11 (corresponding to 8.8 U) and reacted at 30° C. for 16 hours with shaking. After the reaction, the reaction mixture was centrifuged (12,000 rpm, 5 minutes) to obtain an aqueous phase, whose N-benzylpyrrolidine-2-carboxylic acid content is determined as described in Example 2. The optical isomers of N-benzylpyrrolidine-2-carboxylic acid are analyzed by the method described in Example 2. From these results, the production rate (%) (the production rate (%) of N-benzylpyrrolidine-2-carboxylic acid based on each racemic N-benzylpyrrolidine-2-carboxylate as a starting material) and the optical purity of N-benzylpyrrolidine-2-carboxylic acid are calculated.

Example 14

30 µl of ethyl N-benzyl-L-azetidine carboxylates, 1.0 mL of methyl-t-butylether and 1.5 mL of 100 mM potassium phosphate buffer (pH7.0) are placed in a 10 mL screw-capped tube and supplemented with 0.5 mL of the enzyme solution prepared in Example 12 (corresponding to 8.8 U) and reacted at 30° C. for 16 hours with shaking. After the reaction, the reaction mixture is centrifuged (12,000 rpm, 5 minutes) to obtain a methyl-t-butylether phase, whose ethyl N-benzylazetidine-2-carboxylate amount and the optical isomers are analyzed by the methods described below. From the methyl-t-butylether phase thus obtained, methyl-t-butylether was evaporated off under reduced pressure to obtain ethyl (R)-N-benzylazetidine-2-carboxylate.

The present invention provides a novel gene encoding a protein having an excellent catalyst ability for producing the cyclic imino acid (2) as well as a novel method for producing the (S)-cyclic imino acid (2) in a manner of gene engineering technology utilizing the novel gene provided.

What is claimed is:

1. An isolated protein comprising any one of the following amino acid sequences:

(a) the amino acid sequence of SEQ ID NO: 1;

(b) an amino acid sequence of a protein which is capable of hydrolyzing a racemic ethyl N-benzylazetidine-2-carboxylate asymmetrically and producing an (S)-N-benzylazetidine-2-carboxylic acid and which consists of a part of the amino acid sequence of SEQ ID NO: 1;

(c) an amino acid sequence of a protein which is capable of hydrolyzing a racemic ethyl N-benzylazetidine-2-carboxylate asymmetrically and producing an (S)-N-benzylazetidine-2-carboxylic acid and which is encoded by a nucleotide sequence which hybridizes under stringent conditions of between 450 and 900 mM sodium chloride, 45 to 90 mM sodium citrate and a temperature of 65° C., with a DNA sequence consisting of a nucleotide sequence encoding the amino acid sequence of SEQ ID NO: 1;

(d) an amino acid sequence of a protein which is capable of hydrolyzing a racemic ethyl N-benzylazetidine-2-carboxylate asymmetrically and producing an (S)-N-benzylazetidine-2-carboxylic acid and which has an amino acid homology of 80% or higher with the amino acid sequence represented by SEQ ID NO: 1.

2. An isolated protein comprising any one of the following amino acid sequences:

(a) the amino acid sequence of SEQ ID NO: 1;

(b) an amino acid sequence represented by amino acids 35 to 255 of SEQ ID NO: 1;

(c) an amino acid sequence represented by amino acids 79 to 255 of SEQ ID NO: 1;

(d) an amino acid sequence encoded by the nucleotide sequence of SEQ ID NO: 2;

(e) an amino acid sequence encoded by the nucleotide sequence represented by nucleotides 103 to 765 of SEQ ID NO: 2; and, (f) an amino acid sequence encoded by the nucleotide sequence represented by nucleotides 235 to 765 of SEQ ID NO: 2.

3. An isolated protein comprising any one of the following amino acid sequences:

(a) the amino acid sequence of SEQ ID NO: 1;

(b) an amino acid sequence of a protein which is capable of hydrolyzing a racemic ethyl N-benzylazetidine-2-carboxylate asymmetrically and producing an (S)-N-benzylazetidine-2-carboxylic acid and which consists of a part of the amino acid sequence of SEQ ID NO: 1;

(c) an amino acid sequence of a protein which is capable of hydrolyzing a racemic ethyl N-benzylazetidine-2-carboxylate asymmetrically and producing an (S)-N-benzylazetidine-2-carboxylic acid and which is encoded by a nucleotide sequence which hybridizes under stringent conditions of between 450 and 900 mM sodium chloride, 45 to 90 mM sodium citrate and a temperature of 65° C., with a DNA sequence consisting of a nucleotide sequence encoding the amino acid sequence of SEQ ID NO: 1;

(d) an amino acid sequence of a protein which is capable of hydrolyzing a racemic ethyl N-benzylazetidine-2-carboxylate asymmetrically and producing an (S)-N-benzylazetidine-2-carboxylic acid and which has a molecular weight of about 25,000 daltons determined by an SDS-PAGE, and which is obtained from the microorganism *Aspergillus flavus*; and, (e) an amino acid sequence of a protein which is capable of hydrolyzing a racemic ethyl N-benzylazetidine-2-carboxylate asymmetrically and producing an (S)-N-benzylazetidine-2-carboxylic acid and which has an amino acid homology of 80% or higher with the amino acid sequence represented by SEQ ID NO: 1.

* * * * *